US011096674B2

(12) United States Patent
Podilchuk et al.

(10) Patent No.: US 11,096,674 B2
(45) Date of Patent: Aug. 24, 2021

(54) METHOD AND MEANS OF CAD SYSTEM PERSONALIZATION TO PROVIDE A CONFIDENCE LEVEL INDICATOR FOR CAD SYSTEM RECOMMENDATIONS

(71) Applicant: Koios Medical, Inc., New York, NY (US)

(72) Inventors: Christine I. Podilchuk, Piscataway, NJ (US); Ajit Jairaj, Piscataway, NJ (US); Lev Barinov, Piscataway, NJ (US); William Hulbert, Piscataway, NJ (US); Richard Mammone, Piscataway, NJ (US)

(73) Assignee: Koios Medical, Inc., New York, NY (US)

( * ) Notice: Subject to any disclaimer, the term of this patent is extended or adjusted under 35 U.S.C. 154(b) by 0 days.

(21) Appl. No.: 16/324,835

(22) PCT Filed: Aug. 11, 2017

(86) PCT No.: PCT/US2017/046565
§ 371 (c)(1),
(2) Date: Feb. 11, 2019

(87) PCT Pub. No.: WO2018/031919
PCT Pub. Date: Feb. 15, 2018

(65) Prior Publication Data
US 2019/0223845 A1    Jul. 25, 2019

Related U.S. Application Data

(63) Continuation of application No. 15/235,050, filed on Aug. 11, 2016, now Pat. No. 9,536,054.

(51) Int. Cl.
*G06K 9/00* (2006.01)
*A61B 10/00* (2006.01)
(Continued)

(52) U.S. Cl.
CPC ........ *A61B 10/0041* (2013.01); *G06K 9/6262* (2013.01); *G06T 7/0012* (2013.01);
(Continued)

(58) Field of Classification Search
CPC . G06T 2207/30068; G06T 2207/20081; G06T 2207/20092; G06T 7/0012;
(Continued)

(56) References Cited

U.S. PATENT DOCUMENTS 5,260,871 A    11/1993  Goldberg
7,418,119 B2    8/2008  Leichter et al.
(Continued)

FOREIGN PATENT DOCUMENTS

CN         105913086 A      8/2016
WO    WO 2007/138533      12/2007

OTHER PUBLICATIONS

Chao et al, Multi-Label Relevant Vector Machine based Simultaneous Fault Diagnosis, IEEE 2013, ("based on English translation of Abstract only") (Year: 2013).*

(Continued)

*Primary Examiner* — Amara Abdi

(57) ABSTRACT

A method and means to utilize machine learning to train a device to generate a confidence level indicator (CLI). The device is a CAD system that has been initially trained using initial machine learning to recommend classifications for image features presented to the device. Probabilistic classification is utilized to incorporate intermediate values given by a human operator to better indicate a level of confidence of the CAD system's recommendations as to what classes should be associated with certain image features.

14 Claims, 6 Drawing Sheets

(51) Int. Cl.

| | |
|---|---|
| *G06T 7/00* | (2017.01) |
| *G06K 9/62* | (2006.01) |
| *G16H 50/20* | (2018.01) |
| *A61B 6/00* | (2006.01) |
| *A61B 8/08* | (2006.01) |

(52) U.S. Cl.
CPC .............. *G16H 50/20* (2018.01); *A61B 6/502* (2013.01); *A61B 8/0825* (2013.01); *G06T 2207/20081* (2013.01); *G06T 2207/20092* (2013.01); *G06T 2207/30068* (2013.01)

(58) Field of Classification Search
CPC ... A61B 6/502; A61B 8/0825; A61B 10/0041; G06K 9/6262; G16H 50/20
See application file for complete search history.

(56) References Cited

U.S. PATENT DOCUMENTS

| | | | |
|---|---|---|---|
| 7,570,051 | B2 | 8/2009 | Haider |
| 9,536,054 | B1 | 1/2017 | Podilchuk et al. |
| 9,934,567 | B2 | 4/2018 | Podilchuk et al. |
| 9,959,617 | B2 | 5/2018 | Chang et al. |
| 10,339,650 | B2 | 7/2019 | Podilchuk et al. |
| 10,346,982 | B2 | 7/2019 | Podilchuk et al. |
| 2004/0184644 | A1 | 9/2004 | Leichter et al. |
| 2004/0254816 | A1 | 12/2004 | Myers |
| 2005/0010445 | A1* | 1/2005 | Krishnan ............. G06T 7/0012 705/2 |
| 2005/0049497 | A1 | 3/2005 | Krishnan et al. |
| 2005/0059876 | A1 | 3/2005 | Krishnan et al. |
| 2005/0111718 | A1 | 5/2005 | MacMahon et al. |
| 2005/0244041 | A1 | 11/2005 | Tecotzky et al. |
| 2006/0122467 | A1 | 6/2006 | Harrington et al. |
| 2006/0210133 | A1 | 9/2006 | Krishnan et al. |
| 2007/0076957 | A1 | 4/2007 | Wang et al. |
| 2007/0133852 | A1 | 6/2007 | Collins et al. |
| 2007/0167727 | A1 | 7/2007 | Menezes et al. |
| 2009/0034809 | A1 | 2/2009 | Oakley |
| 2009/0034810 | A1 | 2/2009 | Oakley |
| 2009/0093711 | A1 | 4/2009 | Valadez |
| 2010/0121178 | A1* | 5/2010 | Krishnan ............. G06T 7/0012 600/411 |
| 2010/0200660 | A1 | 8/2010 | Moed et al. |
| 2011/0164064 | A1 | 7/2011 | Tanaka et al. |
| 2011/0200227 | A1 | 8/2011 | Bogoni et al. |
| 2012/0088981 | A1 | 4/2012 | Liu et al. |
| 2012/0257804 | A1* | 10/2012 | Zhang .................... A61B 6/563 382/128 |
| 2014/0010430 | A1 | 1/2014 | Chandelier et al. |
| 2014/0066767 | A1 | 3/2014 | Mammone et al. |
| 2014/0122515 | A1* | 5/2014 | Lee ......................... G06F 19/00 707/758 |
| 2016/0109955 | A1 | 4/2016 | Park et al. |
| 2016/0125265 | A1 | 5/2016 | Xie et al. |
| 2016/0133028 | A1 | 5/2016 | Park |
| 2017/0200266 | A1 | 7/2017 | Podilchuk et al. |
| 2017/0200268 | A1 | 7/2017 | Podilchuk et al. |
| 2018/0053300 | A1 | 2/2018 | Podilchuk et al. |
| 2020/0175684 | A1 | 6/2020 | Podilchuk et al. |
| 2020/0184635 | A1 | 6/2020 | Podilchuk et al. |

OTHER PUBLICATIONS

Chuyang et al, ("Improved Mass Detection in 3D Automated Breast Ultrasound Using Region Based Features and Multi-view Information", pp. 2865-2868, IEEE 2014), (Year: 2014).*

Maceij et al, ("individualized computer-aided education in mammography based on user modeling: Concept and preliminary experiments", Med. Phys. 37(3), Mar. 2010) (Year: 2010).*

Search Report for United Kingdom Application No. GB1703624.5, dated Aug. 21, 2017, 4 pages.

Office Action for U.S. Appl. No. 15/200,719, dated Jan. 11, 2018, 23 pages.

Office Action for U.S. Appl. No. 15/200,719, dated Sep. 7, 2018, 26 pages.

International Search Report and Written Opinion for International Application No. PCT/US2017/046565, dated Sep. 12, 2017, 9 pages.

Office Action for U.S. Appl. No. 15/451,086, dated Sep. 11, 2017, 10 pages.

International Search Report and Written Opinion for International Application No. PCT/US2017/047995, dated Nov. 7, 2017, 16 pages.

Baker, J. A. et al., "Breast cancer: prediction with artificial neural network based on BI-RADS standardized lexicon," Radiology Society of North America, Sep. 1995, vol. 196, Issue 3, http://pubs.rsna.org/doi/abs/10.1148/radiology.196.3.7644649.

Barinov, L. et al., "Decision Quality Support in Diagnostic Breast Ultrasound through Artificial Intelligence," IEEE Signal Processing in Medicine and Biology Symposium (SPMB), SPMB-L3.03, Dec. 3, 2016.

Berg, W. A. et al., "Breast-Imaging Reporting and Data System: Inter- and Intraobserver Variability in Feature Analysis and Final Assessment," AJR 2000;174:1769-1777. Retrieved from the Internet: <URL: http://www.ajronline.org>, by Rutgers University on Apr. 8, 2016.

Croskerry, P., "The Importance of Cognitive Errors in Diagnosis and Strategies to Minimize Them," Academic Medicine, Aug. 2003, 78(8):775-780.

Huang, Z. et al., "Beyond cross-entropy: Towards better frame-level objective functions for deep neural network raining in automatic speech recognition," ISCA, Sep. 2014, 1214-1218, http://research.microsofl.com/pubs/230081/IS140944.pdf.

Isaac, L. et al., "Computerized classification can reduce unnecessary biopsies in BI-RADS category 4A lesions," IWDM 2006, LNCS 4046, pp. 76-83, 2006.

Jorritsma, W. et al., "Improving the radiologist-CAD interaction: designing for appropriate trust," Clinical Radiology, 70 (2015) 115-122.

Vinyals, O. et al., "Show and Tell: A Neural Image Caption Generator," arXiv:1411.4555v2 [cs.CV], Apr. 20, 2015, 9 pages.

Extended European Search Report for European Application No. 17840359.8, dated Mar. 10, 2020, 13 pages.

Extended European Search Report for European Application No. 17844275.2, dated Feb. 10, 2020, 11 pages.

Ye, C. et al., "Improved mass detection in 3D automated breast ultrasound using region based features and multi-view information", 2014, 36th Annual International Conference of the IEEE Engineering in Medicine and Biology Society, Aug. 26, 2014, pp. 2865-2868.

Boukerroui, D. et al., "Velocity Estimation in Ultrasound Images: A Block Matching Approach," In: Lecture Notes in Computer Science, C.J. Taylor and J.A. Noble (Eds.): IPMI 2003, LNCS 2732, pp. 586-598 (2003).

Chao, S. et al., "Multi-label relevant vector machine based simultaneous fault diagnosis," 2013 25th Chinese Control and Decision Conference (CCDC), Guiyang, 2013, pp. 4792-4796, (with English Abstract), doi: 10.1109/CCDC.2013.6561801.

Mazurowski, M. et al., "Individualized computer-aided education in mammography based on user modeling: Concept and preliminary experiments," Medical Physics, vol. 37, No. 3, Mar. 2010, pp. 1152-1160.

Office Action for United Kingdom Application No. GB1703624.5, dated Mar. 12, 2021, 2 pages.

* cited by examiner

METHOD AND MEANS OF CAD SYSTEM PERSONALIZATION TO PROVIDE A CONFIDENCE LEVEL INDICATOR FOR CAD SYSTEM RECOMMENDATIONS

CROSS-REFERENCE TO RELATED APPLICATION

This Patent Application is a 371 national stage filing of PCT International Application No. PCT/US2017/046565, filed Aug. 11, 2017, and titled "Method and Means of CAD System Personalization to Provide a Confidence Level Indicator for CAD System Recommendations," which is a continuation of U.S. patent application Ser. No. 15/235,050, filed Aug. 11, 2016, and titled "Method and Means of CAD System Personalization to Provide a Confidence Level Indicator for CAD System Recommendations," the entire contents of each of which is incorporated by reference herein in its entirety.

BACKGROUND

1. Field

The present inventive concept relates generally to medical imaging and analysis; and, more particularly to a system and method to enhance clinical decision making capability within the context of an image reporting and data system (IRADS) for medical diagnosis. The present inventive concept provides a confidence level indication (CLI) for a computer-assisted diagnosis (CAD) system that is programmed to minimize the deviations in recommended clinical actions due to the biases of a group or individual in interpreting the rules of the system.

2. Discussion of Related Art

Each year, over 1,300,000 breast biopsies are performed in the United States and over 4,500,000 breast biopsies are performed worldwide. Of these biopsies, 80% have benign findings. Breast biopsies are traumatic experiences that expose patients to clinical risk, are uncomfortable, and are costly.

A trained medical professional such as a radiologist will generally attempt to identify and classify regions of suspicion within a medical image either manually or by using computer software. The radiologist may then manually characterize each region of suspicion in accordance with a relevant grading system. For example, suspicious regions of interest within the breast may be characterized according to Breast Imaging Reporting and Data Systems (BI-RADS) guidelines. BI-RADS is a widely-accepted risk assessment and quality assurance tool used by radiologists for diagnosing breast cancer using mammography, ultrasound, or MRI. The classification assigned to each region of suspicion may dictate the future course of action. For example, if the region of suspicion is classified as likely malignant, then a biopsy may be ordered. If the region of suspicion is classified as normal, then no further action may be taken. If, however, the region of suspicion is classified as probably benign, then the course of action may be to repeat the test in six months to look for any changes. The BI-RADS reporting methodology includes a standard lexicon and structure for reporting purposes which enables radiologists to provide a succinct review of image based findings and to communicate the results to the referring physician in a clear and consistent fashion with a final assessment and a specific course of action. Structured reporting also helps accelerate report turnaround time (TAT), simplify documentation for billing and regulatory compliance, and ease the process of data extraction for utilization review, quality assurance, and research. Through medical audit and outcome monitoring, the system provides important mechanisms for peer review and quality assurance data to improve the quality of patient care. Results compiled in a standardized manner permit the maintenance and collection analysis of demographic and outcome data.

The success of BI-RADS since its inception for mammography in 1993 has spurred the introduction of many more similar checklist-based systems for various medical image reporting and data systems. A partial list of similar reporting and data systems include Prostate Imaging-Reporting and Data System (PI-RADS), Thyroid Imaging Reporting and Data System (TI-RADS), Liver Imaging Reporting and Data System (LI-RADS), and Lung-RADS for prostate, thyroid, liver and lung cancer diagnosis, respectively.

The basic BI-RADS Assessment Categories are:
1: Negative,
2: Benign,
3: Probably benign,
4. Suspicious, and
5: Highly suggestive of malignancy.

There is also a category 0 (BI-RADS 0) and a category 6 (BI-RADS 6). A BI-RADS 0 indicates an incomplete classification which warrants either an effort to ascertain prior imaging for comparison or to call the patient back for additional views, higher quality films or additional imaging modalities. A BI-RADS 6 indicates a proven malignancy previously proven by biopsy.

The BI-RADS 4 classification is frequently divided into sub-categories of:
4A: low suspicion for malignancy,
4B: moderate suspicion for malignancy, and
4C: highly suspicious for malignancy.

The recommended patient management provided by the BI-RADS system is: if the region of interest is classified as suspicious or highly suspicious, i.e., BI-RADS 4 or BI-RADS 5, then a biopsy should be ordered. If the region of suspicion is classified as normal or benign, i.e., BI-RADS 1 or BI-RADS 2, then no further action may be taken. If, however, the region of suspicion is classified as probably benign, i.e., BI-RADS 3, then the recommendation is a 6-month follow-up to look for any changes. The BI-RADS score is a statistic that is correlated with malignancy and not a deterministic measure of malignancy. It has been shown that category 3 (less than 2 percent risk of malignancy) or category 4 (probability of cancer, ranging from 3 percent to 94 percent) lesions are considered different degrees of malignant breast lesions. This is especially true for hyperplastic nodules in category 3, which are considered to be uncertain ones. Such lesions do not have obvious characteristics of benign lesions, but they are still considered subjectively as category 3 lesions. There are 1-2 non-benign characteristics of category 4 lesions, but the American College of Radiology does not provide any detailed guidance. This leads to poor inter-observer consistency in classification with resulting discrepancies from the ideal use of the BI-RADS system. In addition, Category 4a typically consists of 90% to 98% benign lesions, 4b consists of 50% to 90% benign lesions and 4c consists of 5% to 50% benign lesions and BI-RADS 5 has 0% to 5% benign lesions but all must go to biopsy. Therefore, as many as 80% of the biopsies performed on the patients with a category BI-RADS 4 or BI-RADS 5 are found to be benign.

Computer-aided diagnosis (CAD) systems have the potential to improve radiologists' diagnostic performance. However, in practice radiologists have difficulty knowing when to accept or decline the recommendations made by a CAD system.

It is with these observations in mind, among others, that various aspects of the present inventive concept were conceived and developed.

SUMMARY

The present inventive concept provides a computerized system configured to utilize probabilistic classification incorporating intermediate values given by a human operator in order to better indicate a level of confidence in a CAD recommendation system.

The aforementioned may be achieved in an aspect of the present inventive concept by providing a method of personalizing a diagnosis assistance system. The method may include the step of utilizing machine learning to train a device to provide a confidence level indication (CLI) for computer-assisted diagnosis (CAD) system recommendations. Such training may include the step of accessing a plurality of training image features. Each of the plurality of training image features may be associated with known classes of a plurality of classes. The known classes may correspond to known correct diagnostic decisions for each of the training image features.

Such training may further include the step of accessing a plurality of initial clinician recommended diagnostic decisions from at least one operator corresponding to each of the plurality of training image features. Each of the plurality of initial clinician-recommended diagnostic decisions may include a clinician confidence factor.

Such training may further include the step of accessing a plurality of CAD system recommended diagnostic decisions corresponding to each of the plurality of training image features. Each of the plurality of CAD system-recommended diagnostic decisions may include a classifier output score or a combination of the ensemble of scores.

Such training may further include the step of accessing a subset of the plurality of initial clinician-recommended diagnostic decisions corresponding to a subset of the plurality of training image features. The subset of the plurality of initial clinician-recommended diagnostic decisions may differ with respect to certain CAD system-recommended diagnostic decisions corresponding to the subset of the plurality of training image features.

Such training may further include the step of generating a function that defines a CLI score for each of the certain CAD system-recommended diagnostic decisions corresponding to the subset of the plurality of training image features.

The method may further include the step of utilizing initial machine learning to initially train the device, by providing an initial training data set associated with a series of training images. At least a portion of the initial training data set may include image features associated with initial known classes of the plurality of classes. The plurality of classes may be associated with initial predetermined possible clinical actions. The method may further include the step of determining a cost function of weighted error terms based on results of the providing of the initial training data set to the device. The method may further include the step of weighting and/or penalizing certain parameters of the cost function for certain image feature values associated with known examples of clinical significance that are predetermined as being important to diagnose.

The method may further include the step of receiving a selected image by an interface. The selected image may include an image feature. The method may further include the step of utilizing the device to give a specific clinical action, by (i) extracting at least one image feature value from the selected image, and/or (ii) applying the at least one image feature value to the device trained using the weighted cost function to identify a class from the plurality of classes. The device may be trained using the initial machine learning before utilizing machine learning to train the device to provide the CLI for the computer-assisted diagnosis (CAD) system recommendations. The CLI score for each of the certain CAD system-recommended diagnostic decisions corresponding to the subset of the plurality of training image features may be unique to image features of a particular type and/or unique to the at least one operator. One or more parameters of the function may include the clinician confidence factor, the classifier output score, and/or the known correct diagnostic decisions for each of the subset of the plurality of training image features. The step of generating the function that defines the CLI score may include providing a local area of an image where the CAD system weighed its confidence more heavily in its recommendation.

The method may further include the step of periodically repeating, e.g., annually, one or more phases or training steps of the CLI, e.g., an initial training phase to adapt to any learned behavior of a user, e.g., a radiologist, over a period of time. The learned behavior may be a product of using the CDI/CAD system over the period of time, e.g., an improved ability to correctly detect and/or diagnose cancer and/or other learning experiences relative to diagnostic image analysis that the radiologist might have acquired over the period of time. A subset of the plurality of initial clinician-recommended diagnostic decisions corresponding to a subset of the plurality of training image features may further include an initial decision profile and/or a final decision profile by a specific operator, a plurality of specific operators, an institution, a locale, a workflow position, and/or an aggregation of final decisions made by a plurality of operators including to be utilized with the function at defines a CLI score for each of the certain CAD system-recommended diagnostic decisions corresponding to the subset of the plurality of training image features. In other words, the initial scores of an individual or group are recorded following their scores after seeing a CAD recommender score. These scores may be used to help train the CLI or function associated with the same to estimate the odds of a trained CAD device/system being correct over the individual or group's decisions for cases similar to each one seen during training.

Each of the plurality of classes may be associated with different categories of a Breast Imaging Reporting and Data System (BI-RAD) lexicon. Each of the plurality of training image features image may include pixel values and/or a subset of pixel values associated with a region of interest for a legion. The function may be based on or factor one or more intermediate values given by an operator and/or CAD system recommendations to compute the CLI score. The function may utilize a probabilistic classification while incorporating intermediate values given by a human operator in order to better indicate a level of confidence of CAD systems recommendations as defined by the CLI score.

The aforementioned may be achieved in another aspect of the present inventive concept by providing a method of training a diagnosis assistance system. The method may include the step of utilizing machine learning to train a device to provide a confidence level indication (CLI) for computer-assisted diagnosis (CAD) system recommendations. The training may include the step of accessing at least one training image feature associated with a known class corresponding to a known correct diagnostic decision for the training image feature. The training may further include the step of accessing a clinician-recommended diagnostic decision from at least one operator corresponding to the training image feature. The training may further include the step of accessing a CAD system-recommended diagnostic decision corresponding to the training image feature comprising a classifier output score or a combination of the ensemble of scores. The CAD-system recommended diagnostic decision may differ from the clinician-recommended diagnostic decision. The training may further include the step of generating a function that defines a CLI score for the CAD system-recommended diagnostic decision. One or more parameters of the function may include a clinician confidence factor, the classifier output score, and/or the known correct diagnostic decision for the training image feature. The clinician-recommended diagnostic decision may define an intermediate value given by the at least one operator.

The aforementioned may be achieved in another aspect of the present inventive concept by providing a diagnosis assistance training system or apparatus. The apparatus may include at least one computing device. The computing device may be operable to be trained via machine learning to generate a recommended class based on one or more image features using a cost function of one or more weighted terms, with one or more parameters of the cost function being weighted and/or penalized for certain image features associated with predetermined known examples of clinical significance. Additional machine learning may be applied to the computing device. Such additional machine learning may include a plurality of clinician diagnostic decisions accessed by the computing device from an operator corresponding to each of a plurality of training image features. Each of the plurality of initial clinician diagnostic decisions may include a clinician confidence factor. Such additional machine learning may include a plurality of CAD system diagnostic decisions corresponding to each of the plurality of training image features accessed by the computing device. Each of the plurality of CAD system diagnostic decisions may include a classifier output score or a combination of the ensemble of scores. A subset of the plurality of clinician diagnostic decisions may correspond to a subset of the plurality of training image features that differ with respect to certain CAD system diagnostic decisions for the plurality of training image features accessed by the computing device. Such additional machine learning may include a function executed by the computing device that may define a CLI score for each of the certain CAD system diagnostic decisions corresponding to the subset of the plurality of training image features. The function may be defined as: P (c/X; and Z; and W; and Q), to compute a probability that being in class c, given a feature vector X, and the operator selects a label Z, and the CAD system recommendation is defined by label W, with a ground known truth defined as label Q. The CLI score may define a probability of the computing device correctly generating the recommended class by taking into account intermediate values given by the at least one operator using probabilistic classification.

BRIEF DESCRIPTION OF THE DRAWINGS

The foregoing and other objects, features, and advantages of the present inventive concept set forth herein should be apparent from the following description of particular embodiments of those inventive concepts, as illustrated in the accompanying drawings. The drawings depict only typical embodiments of the present inventive concept and, therefore, are not to be considered limiting in scope.

Figure 1:
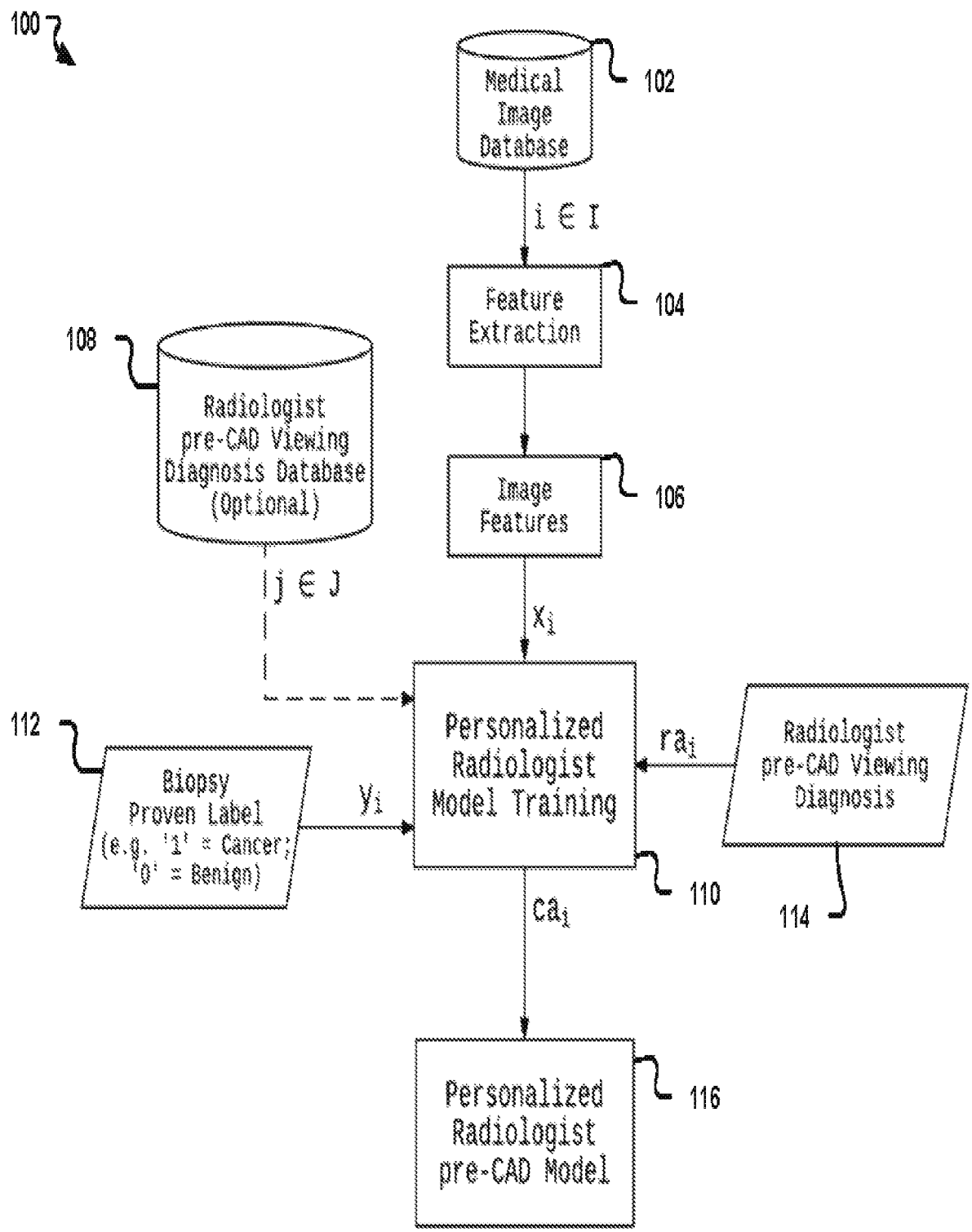
FIG. 1 is an exemplary process flow, according to aspects of the present inventive concept.

The drawing figures do not limit the present inventive concept to the specific embodiments disclosed and described herein. The drawings are not necessarily to scale, emphasis instead being placed on clearly illustrating principles of certain embodiments of the present inventive concept.

DETAILED DESCRIPTION

The following detailed description references the accompanying drawings that illustrate various embodiments of the present inventive concept. The illustrations and description are intended to describe aspects and embodiments of the present inventive concept in sufficient detail to enable those skilled in the art to practice the present inventive concept. Other components can be utilized and changes can be made without departing from the scope of the present inventive concept. The following detailed description is, therefore, not to be taken in a limiting sense. The scope of the present inventive concept is defined only by the appended claims, along with the full scope of equivalents to which such claims are entitled.

I. Terminology

In the description, terminology is used to describe features of the present inventive concept. For example, references to terms "one embodiment," "an embodiment," "the embodiment," or "embodiments" mean that the feature or features being referred to are included in at least one aspect of the present inventive concept. Separate references to terms "one embodiment," "an embodiment," "the embodiment," or "embodiments" in this description do not necessarily refer to the same embodiment and are also not mutually exclusive unless so stated and/or except as will be readily apparent to those skilled in the art from the description. For example, a feature, structure, process, step, action, or the like described in one embodiment may also be included in other embodiments, but is not necessarily included. Thus, the present inventive concept may include a variety of combinations and/or integrations of the embodiments described herein. Additionally, all aspects of the present disclosure as described herein are not essential for its practice.

The term "algorithm" refers to logic, hardware, firmware, software, and/or a combination thereof that is configured to perform one or more functions including, but not limited to, those functions of the present inventive concept specifically described herein or are readily apparent to those skilled in the art in view of the description. Such logic may include circuitry having data processing and/or storage functionality. Examples of such circuitry may include, but are not limited to, a microprocessor, one or more processors, e.g., processor cores, a programmable gate array, a microcontroller, an application specific integrated circuit, a wireless receiver, transmitter and/or transceiver circuitry, semiconductor memory, or combinatorial logic.

The term "logic" refers to computer code and/or instructions in the form of one or more software modules, such as executable code in the form of an executable application, an application programming interface (API), a subroutine, a function, a procedure, an applet, a servlet, a routine, source code, object code, a shared library/dynamic load library, or one or more instructions. These software modules may be stored in any type of a suitable non-transitory storage medium, or transitory storage medium, e.g., electrical, optical, acoustical, or other form of propagated signals such as carrier waves, infrared signals, or digital signals. Examples of non-transitory storage medium may include, but are not limited or restricted to a programmable circuit; a semiconductor memory; non-persistent storage such as volatile memory (e.g., any type of random access memory "RAM"); persistent storage such as nonvolatile memory (e.g., read-only memory "ROM", power-backed RAM, flash memory, phase-change memory, etc.), a solid-state drive, hard disk drive, an optical disc drive, or a portable memory device. As firmware, the executable code is stored in persistent storage.

The term "user" is generally used synonymously herein to represent a user of the system and/or method of the present inventive concept. For purposes herein, the user may be a clinician, a diagnostician, a doctor, a technician, a student, and/or an administrator.

The terms "identified," "processed," and "selected" are generally used synonymously herein, regardless of tense, to represent a computerized process that is automatically performed or executed by the system in one or more processes via at least one processor.

The acronym "CAD" means Computer-Assisted Diagnosis.

The term "client" means any program of software that connects to a CAD lesion application.

The term "server" typically refers to a CAD lesion application that is listening for one or more clients unless otherwise specified.

The term "post-processing" means an algorithm applied to an inputted ultrasound image.

The acronym "PACS" means Picture Archival and Communication System.

The acronym "GSPS" means Grayscale Softcopy Presentation State.

The acronym "DICOM" means Digital Imaging and Communications in Medicine.

The acronym "UI" means User Interface.

The acronym "PHI" means Private Health Information.

The term "computerized" generally represents that any corresponding operations are conducted by hardware in combination with software and/or firmware.

The term "ensemble methods" means multiple learning algorithms to obtain better performance that could be obtained from any of the constituent learning algorithms.

The term "stacking" means training a learning algorithm to combine the predictions of several other learning algorithms. Stacking may also be referred to as stacked generalization.

The term "combiner" means an algorithm trained to make a final prediction using all of the predictions of other algorithms as additional inputs.

The term "diversity" means variation among ensemble methods/models. Many ensemble methods seek to promote diversity among the models they combine. More random algorithms (such as random decision trees) can be used to produce a stronger ensemble than very deliberate algorithms (such as entropy-reducing decision trees). Using a variety of strong learning algorithms (diversity), however, has been shown to be more effective than using techniques that attempt to dumb-down models in order to promote diversity.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As the present inventive concept is susceptible to embodiments of many different forms, it is intended that the present disclosure be considered as an example of the principles of the present inventive concept and not intended to limit the present inventive concept to the specific embodiments shown and described.

II. Reference to U.S. Patent Application Ser. No. 15/200,719

Aspects of the present inventive concept provide a system and method that utilizes a preexisting Computer-Assisted Diagnosis (CAD) recommendation system implemented on a computing device as described in the related U.S. patent application Ser. No. 15/200,719 incorporated herein by reference. The CAD recommendation system of U.S. patent application Ser. No. 15/200,719 is specially programmed to minimize discrepancies between recommended clinical actions to address image features taken from an individual or specific group of experts; and optimum clinical actions based on correlation with proven or evidence-based data. The CAD recommendation system of U.S. patent application Ser. No. 15/200,719 reduces the number of erroneous clinical actions such as biopsies based on the operator's error profile.

Aspects of the previous CAD recommendation system utilize machine learning to train a computing device to suggest clinical decisions about image features. A training data set associated with a series of training images may be applied to a computing device. The series of training images may comprise medical images, showing a particular area of the human body, such as a human breast. In particular, the training images may comprise images of a portion of a breast with malignant or benign lesions. Each of the images, depending upon the lesion shown, may comprise different characteristics, such as color, shading, and the like. At least a portion of the training data set may comprise image features, from the training images, that are associated with known classes of a plurality of classes (of a medical lexicon). In other words, the image features have been proven to be linked to certain classes of a medical lexicon. For example, a class 1 of a BI-RADS lexicon may be associated with or assigned to an image feature of a first training image, and a class 2 of a BI-RADS lexicon may be associated with or assigned to an image feature of a second training image. Image features may be vectors, or other values of a particular image, such as a medical image. In other words, at least a portion of the training data set may provide examples to the computing device about when images features should be assigned to one or more classes of a medical lexicon.

Each of the classes of the medical lexicon may be associated with or correspond to predetermined possible clinical actions. In other words, it may be predetermined that when an image feature falls within a particular class, a certain clinical decision should be recommended that is specific to that class. Clinical actions may comprise, for example, certain tasks or procedures that should be taken based on image features. As an example, a clinical action may comprise performing a biopsy on a lesion to remove a tissue sample of the lesion and submit the tissue sample for testing and analysis. Another clinical action may comprise following up with a patient and lesion after a predetermined period of time, such as six months.

A cost function of weighted terms may be determined based upon the training set data as applied to the computing device. In addition, certain parameters of the cost function may be weighted for certain image feature values associated with known examples of clinical significance that are predetermined as being important to diagnose. For example, the certain parameters may be weighted to account for a difficulty of a radiologist or other clinician to accurately diagnose an image feature as belonging to one or more of the plurality of classes.

In one specific embodiment, the described machine learning may be utilized to train a computing device to give clinical decisions in the specific context of possible cancer diagnosis. A training data set in the form of a preselected group of data patterns, which identifies relationships between one or more image features and known correct BI-RAD classifications, may be presented to the computing device for classification. The training data set may identify, for example, that an image feature (of e.g. a lesion) that appears to the human eye as having a particular texture, shape, component/components, shade, color, or other visual characteristic that has been deemed to fall within class 4 according to a BI-RAD lexicon. The image feature may further comprise a particular value (of a pixel, group of pixels, or a function of pixels or group of pixels); e.g. the training data set identifies for the computing device a particular value (feature value) of one or more pixels (or a function of one or more pixels) associated with each image. As such, the training data set further identifies for the computing device feature values or a set of feature values that are associated with images that have been deemed or predetermined (based e.g. on clinical evidence) to fall within one or more BI-RAD classes according to an individual radiologist, or a group of radiologist. In addition, the biopsy proven classification (as to whether the lesion is cancerous or benign) is known.

An actual output produced by the computing device, in response to a training image, may be compared with the known biopsy proven result, with reference to a cost function. In one embodiment, it may be ideal to minimize such a cost function, to minimize the errors outputted by the computing device regarding how image features should be classified with respect to the radiologist or group of radiologists and their selection of the class of a BI-RAD lexicon for the image. Aspects of this comparison may be utilized to adjust certain parameters of the computing device and/or the cost function, such as weights, biases, or penalty functions added to the error terms. In addition, certain parameters of the cost function may be weighted for certain image feature values associated with known examples of clinical significance that are predetermined as being important to diagnose. For example, the certain parameters may be weighted or penalized to account for a difficulty of a radiologist or other clinician to accurately diagnose an image feature as belonging to one or more of the plurality of classes which may be especially important where the clinician is faced with a decision as to whether or not to recommend a biopsy for a lesion. The above process may be repeated until the cost function, averaged over a suitable second preselected group of data patterns or validation set, is minimized. In such an embodiment, training of the computing device to give clinical actions for BI-RAD lesions may be deemed complete when subsequent test data is presented to the computing device, the computing device generates an output on that test data, and a comparison between the output and known correct results yields a difference or value that is within a predetermined acceptable margin. The trained computing device may be implemented for a variety of related applications such as training the computing device to generate decisions in the context of radiology, ultrasound, and the like. The trained computing device may be one element of the CAD recommendation system.

Aspects of the CAD recommendation system utilize the machine learning/training of the training phase described above to recommend classifications for new images that have not already been diagnosed; the classifications corresponding to certain CAD-recommended clinical decisions for the image features. A new selected image may be received by the computing device of the CAD recommendation system using an interface. The computing device may scan the selected image, retrieve image features from the selected image, extract values from the selected image, and match the values to predetermined values that the computing device has been programmed to recognize as being associated with lesions or other abnormalities (as learned during the above training phase). In either case, a selected image comprises at least one image feature is made accessible to the computing device for analysis.

The computing device may extract at least one image feature value from the selected image. The selected image feature value may be associated with a numeric value and may, in some embodiments, be a pixel value or set of pixel values. Extracting a value from a selected image feature in this fashion breaks down an image feature into data understandable by the computing device, and, data that can be utilized with one or more cost functions or other functions developed during machine learning.

The computing device of the CAD recommendation system is utilized by applying the at least one feature value to the computing device which has been trained using the weighted cost function. The computing device then outputs a class from the plurality of classes as defined during the machine learning process. The weighted or penalty based training phase of the CAD system enhances the probability that the CAD system will give a correct score when the operator is more likely to be incorrect. The weighting or penalty function are used to enhance the CAD error profile be diverse from the operator by putting more weight on those errors typically made by the user or users. Alternatively the error terms that are most likely to be made by operator(s) are penalized to enhance their being corrected in the operation of the resulting CAD system. For example, for a given image of a biopsy proven benign image, the computing device may output a score equivalent to a BI-RAD category of 2 which indicates the lesion is benign, however, this same image might be one that is most likely to be categorized as a BI-RADS 4 by the operator indicating that the image feature value is associated with a lesion that is suspicious and should be subject to further diagnosis. Thus, if the radiologist followed the CAD system's recommendation rather than their initial diagnosis they could eliminate this unnecessary biopsy.

III. General Architecture of a CLI System

CAD recommendation systems, such as the CAD recommendation system of U.S. patent application Ser. No. 15/200,719 incorporated herein typically perform with error rates which are similar to expert radiologists. When a CAD recommendation system outputs a class for an image classification, the class corresponding to a CAD-recommended diagnostic decision for the image feature, and that CAD-recommended clinical decision is consistent with an initial clinician recommended diagnostic decision, an operator (or other user) who generates the initial clinician-recommended diagnostic decision is provided with additional confidence in their diagnosis of the image feature. However, when the CAD-recommended diagnostic decision is not consistent with the initial clinician-recommended diagnostic decision, the operator is forced to make a decision to select between unaided diagnosis (the initial clinician-recommended diagnostic decision that does not take into account a recommendation from a CAD system); and the CAD-recommended diagnostic decision.

The operator may then make a final decision based on confidence in the operator's initial diagnostic decision as compared to the operator's confidence in the CAD-recommended clinical decision. If the operator feels more confident in their own opinion than the CAD system's ability, the operator will be biased towards declining the CAD system's recommendation. On the other hand if the operator has more confidence in the CAD system than their own ability they will be biased towards accepting the CAD system's recommendation. This bias due to the perceived reliability or lack of reliability limits the performance of the combination of CAD and radiologist/operator in the decision making process within every step of the diagnostic workflow.

Ideally, a CAD system will differ from the opinion of an operator such as a radiologist only when the radiologist is incorrect and the CAD system will be able to correct the radiologist. In addition, in an ideal case the CAD system would always agree when the radiologist is correct. However, the radiologist will sometimes be correct and the CAD system will be incorrect. An optimal decision making process could be obtained if the radiologist could have some additional measure of the confidence in the recommendation given by the CAD system. Standard output values of classifiers used in machine learning can be only be interpreted as probabilities under very limited conditions that are rarely met in practice.

The present inventive concept is operable to solve this problem and help the radiologist decide when to accept the CAD recommendation over the initial opinion of the radiologist when the opinion of the radiologist differs with respect to the CAD system recommendation for a particular image/image feature. The present inventive concept addresses this problem by collecting training data while the radiologist employs the CAD system on a database of true data. The training session serves the purpose of familiarizing the radiologist with CAD systems strengths and weaknesses as well as collecting data as to when the CAD system can help correct the radiologist's initial decision. The training data is used to train a predictive model which provides a confidence score for particular CAD system recommendations by the CAD recommendation system. The predictive model gives a score which represents the likelihood of a CAD recommendation being correct given the image data and previous performance of a radiologist. The radiologist can use the personalized confidence score to help decide when it would best to defer to the CAD system. The present inventive concept allows radiologists to calibrate their trust in the CAD system more effectively.

A CAD recommendation system may be trained to have errors which complement the errors made by the radiologist or radiologists who will use the system. The CAD system may be trained so as to more heavily penalize the errors made by the radiologists to provide a CAD system with errors that complement those of the radiologist. The present inventive concept utilizes machine learning/training to further enhance or tune a CAD recommendation system. The present inventive concept provides a method and means whereby the operator (for example a radiologist) is trained to learn to understand when they should trust the CAD system with more confidence than their initial opinion. The operator may be asked to diagnose a set of pre-stored cases based on observing a set of appropriate medical image data. The CAD system will provide a second opinion. The radiologist will be free to change their original opinion based on the CAD recommendation or decline the recommendation. The true diagnosis may be then be displayed along with images of similar cases to help the operator learn by example which cases the operator could benefit from by using the CAD systems recommendation and which cases the operator needs less help from the CAD system. This training phase may be used to form a statistical or predictive model of the confidence level indicator (CLI).

The CLI's purpose is to determine, in cases of disagreement between the CAD system and an operator, which is more likely to be correct, given the case data, and the tendencies and potential biases of each. To this purpose, the CLI's parameters are determined by taking into consideration radiological data, the true (biopsy proven) diagnosis of that data, the CAD system's interpretation of that data, the operator's interpretation of that data, and the change in the operator's interpretation of the data when influenced by the CAD system. The true diagnosis of the data, in this description, can refer to the biopsy proven diagnosis of the case in question.

The operator's interpretation of the data can be obtained using many methods, some of which may include some combination of the following:

1) Direct labels—In this scenario, the operator is tasked with estimating the likelihood of malignancy of a set of lesions. These labels, in the context of their respective cases, are used to inform the CLI of the operator's predispositions. In so doing, the CLI is personalized to that operator.
2) Consensus labels—Similar to the previous scenario, however, many operators are considered. The CLI is then designed around labels determined by some measure of their consensus. In this case the CLI trades personalization for generality over a multitude of operators.
3) Operator Models—Rather than directly using the operator's labels to influence the CLI, they are first used to construct a model of the operator's decision making. This model can then be used to generate large numbers of simulated-operator labels, and obviates the need for having the operator manually label many cases.
4) Multi-operator Models—An extension of method 3, where many operators' behaviors are modeled, rather than a single one. This can be achieved by modeling the consensus of many operators, and/or considering the consensus of many operator-models.
5) Fine-tuned Operator Models—This method compromises between the personalized approach of method 3 and the generalized approach of method 4. In order to do so, a general multi-operator model is first developed. This model can be considered a baseline, which can then be fine-tuned to follow the predilections of an individual operator to whatever extent is deemed optimal.

6) Archetypical Operator Models—This method extends the either of the previous 2. In this incarnation, several models are pre-trained, and represent different operator archetypes. An individual operator's behavior can be matched to the model which most closely mirror's their behaviors. The archetypical model can then be used directly, or further fine-tuned to the user.

The previously mentioned factors may be used to resolve disagreements between the CAD and operator in the most optimal manner. This resolution can be considered a measure of confidence in the CAD's decision with respect to an operator of population of operators.

Aspects of the present inventive concept may be described with reference to the flow chart 100 of FIG. 1. Flow chart 100 illustrates pre-CAD training. As shown in block 102, a plurality of training images may be accessed from medical image database. The training images may depict areas of the human body that have characteristics that may indicate an ailment, injury, or affliction. For example, the training images may include images of a portion of a breast that need to be diagnosed to determine whether the portion shown indicates a possible cancerous region. In block 104, a feature extraction process may be implemented. In block 106, a plurality of image features may be extracted from the training images. In block 110, an operator, such as a radiologist or other clinician, may undergo personalized radiologist model training. Specifically, the operator may recommend a diagnostic decision, or a pre-CAD viewing diagnosis as shown in block 114, for each of at least a portion of the image features extracted from the training images. A personalized radiologist/operator pre-CAD model, as shown in block 116, may be generated that is specific to the operator (or group of operators) comprising data about when the specific operator makes an erroneous diagnostic decision; i.e., a decision that differs from a known proven diagnostic decision (as shown in block 112). The personalized radiologist/operator pre-CAD model of block 116 may help to identify for what types of image features the specific operator tends to make an erroneous decision, i.e., a decision that differs from a known correct diagnostic decision. Importantly, the flow chart 100 of FIG. 1 illustrates the personalized radiologist/operator pre-CAD model of block 116 that is derived without the operator having viewed CAD data. In other words, the operator in FIG. 1 undergoes pre-CAD training to develop the personalized radiologist/operator pre-CAD model of block 116.

FIG. 1 further shows an optional radiologist pre-CAD viewing diagnosis database (pre-CAD database) 108. The pre-CAD database may be utilized to train an operator (e.g. radiologist) before actually measuring the performance of the operator with the personalized radiologist model training of block 110. As such, the pre-CAD database 108 may assist to help the operator to better understand the functionality of a CAD system (that recommends diagnostic decisions during actual training).

Figure 2:
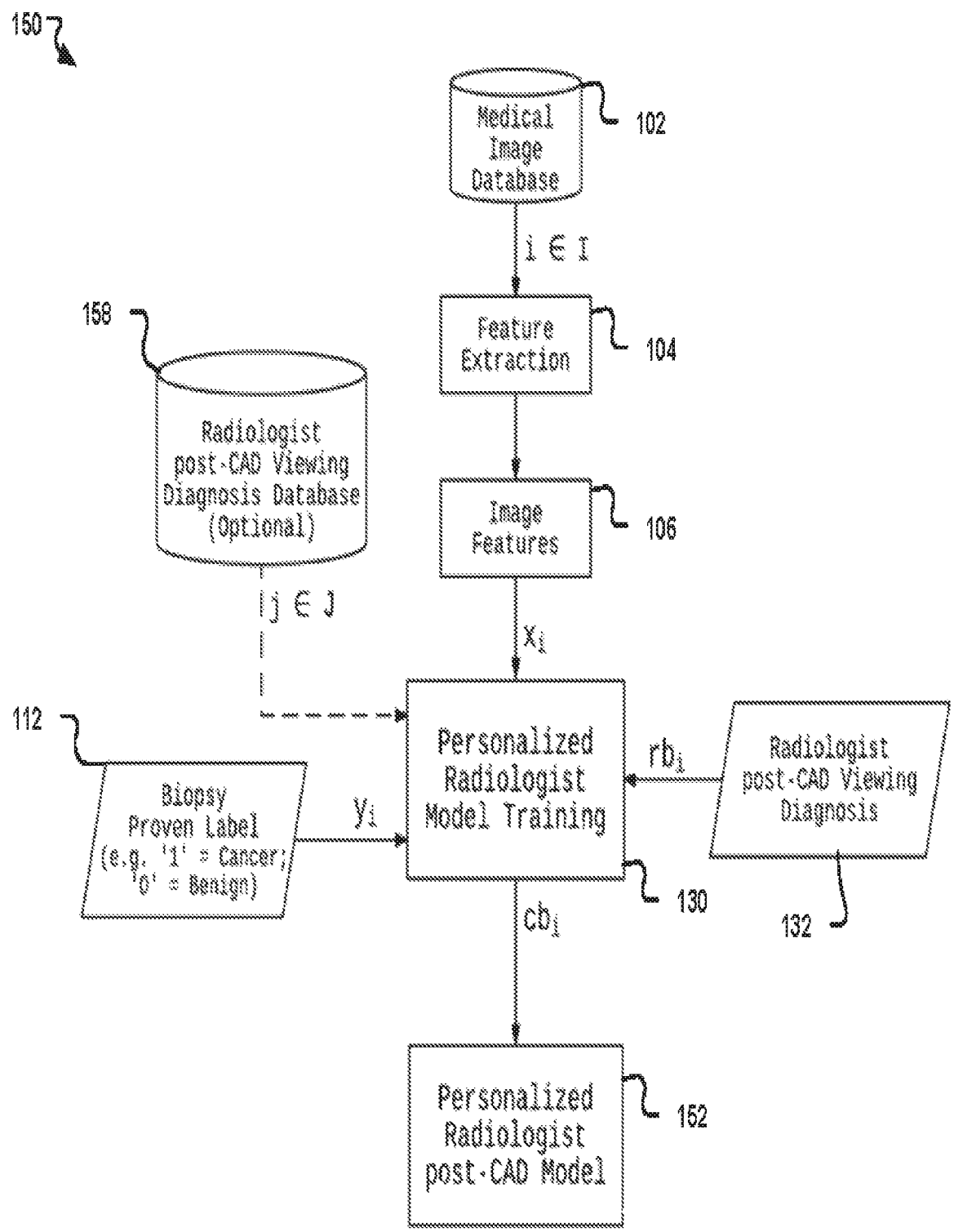
FIG. 2 is an exemplary process flow, according to aspects of the present inventive concept.

FIG. 2 illustrates a flow chart for a training process similar to FIG. 1. The flow chart indicates post-CAD viewing training, i.e., analyzing diagnostic decisions of the operator post-CAD viewing. Similar to FIG. 1, in block 102, a plurality of training images may be accessed from medical image database. The training images may depict areas of the human body that have characteristics that may indicate an ailment, injury, or affliction. For example, the training images may include images of a portion of a breast that need to be diagnosed to determine whether the portion shown indicates a possible cancerous region. In block 104, a feature extraction process may be implemented. In block 106, a plurality of image features may be extracted from the training images.

FIG. 2 further shows an optional radiologist pre-CAD viewing diagnosis database (pre-CAD database) 158. The pre-CAD database may be utilized to train an operator (e.g. radiologist) before actually measuring the performance of the operator with the personalized radiologist model training of block 130. As such, the pre-CAD database 158 may assist to help the operator to better understand the functionality of a CAD system (that recommends diagnostic decisions during actual training).

In block 130, an operator, such as a radiologist or other clinician, may undergo personalized radiologist model training. Specifically, the operator may recommend a diagnostic decision, or a post-CAD viewing diagnosis as shown in block 132, for each of at least a portion of the image features extracted from the training images. A personalized radiologist/operator post-CAD model, as shown in block 152, may be generated that is specific to the operator (or group of operators) comprising data about when the specific operator makes an erroneous diagnostic decision; i.e., a decision that differs from a known proven diagnostic decision (as shown in block 112); and, when the operator makes the decision despite having access to a CAD decision for the same image feature. The personalized radiologist/operator post-CAD model of block 152 may help to identify for what types of image features the specific operator tends to make an erroneous decision, i.e., a decision that differs from a known correct diagnostic decision. Importantly, the flow chart 150 of FIG. 2 illustrates the personalized radiologist/operator post-CAD model of block 152 that is derived with the operator having viewed CAD data. In other words, the operator in FIG. 2 undergoes post-CAD training to develop the personalized radiologist/operator pre-CAD model of block 152.

Figure 3:
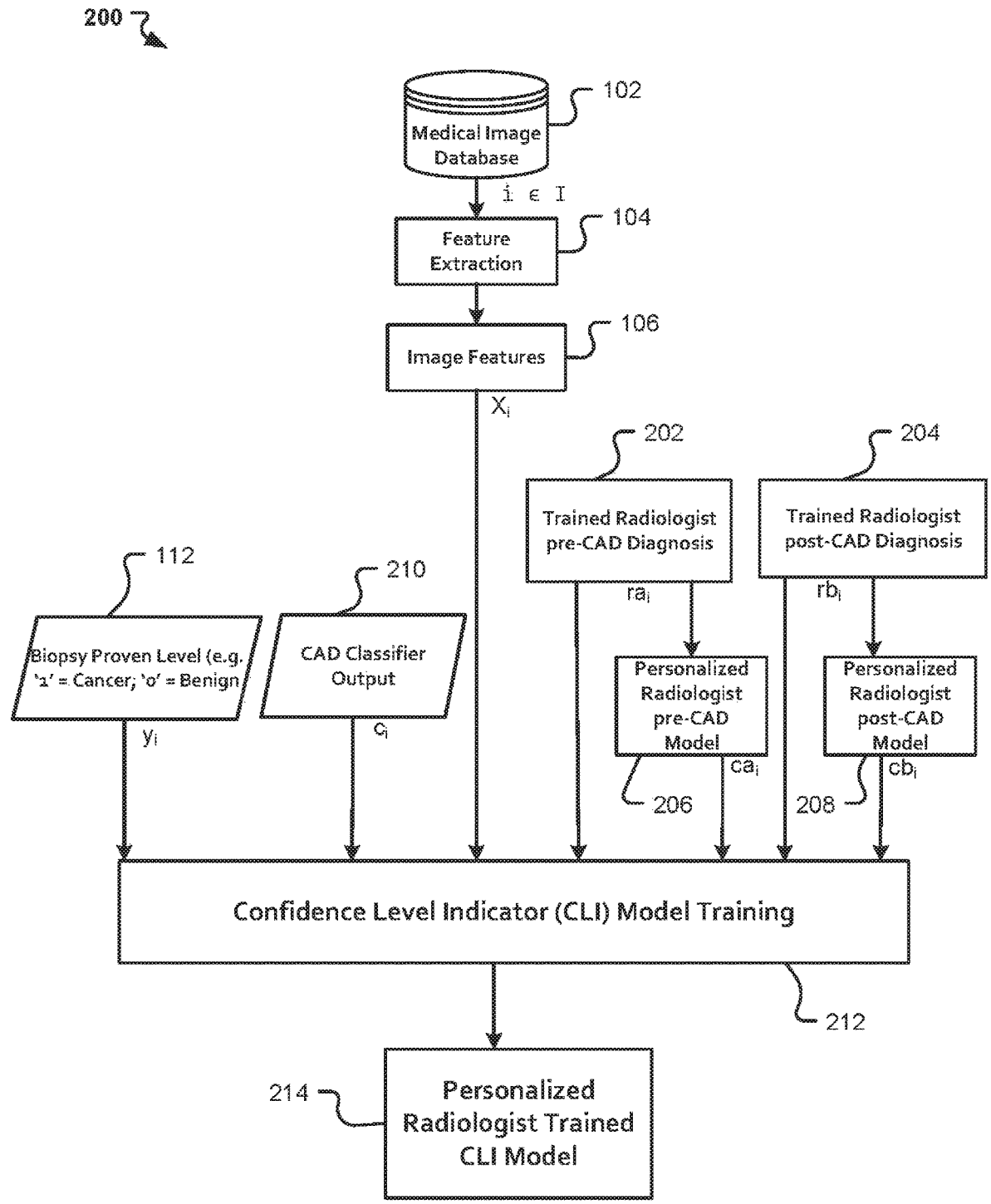
FIG. 3 is an exemplary process flow, according to aspects of the present inventive concept.

FIG. 3 illustrates another flow chart 200 for CLI model training; the output being a personalized operator/radiologist trained CLI model as shown in block 214. Similar to FIGS. 1 and 2, in block 102, a plurality of training images may be accessed from medical image database. The training images may depict areas of the human body that have characteristics that may indicate an ailment, injury, or affliction. For example, the training images may include images of a portion of a breast that need to be diagnosed to determine whether the portion shown indicates a possible cancerous region. In block 104, a feature extraction process may be implemented. In block 106, a plurality of image features may be extracted from the training images.

As shown, confidence level indicator model training may take as inputs known correct diagnostic decision labels of block 112, a CAD system classifier output of block 210, a trained radiologist pre-CAD diagnosis of block 202, a personalized radiologist pre-CAD model of block 206, a trained radiologist post-CAD diagnosis of blocks 204, and a personalized radiologist post-CAD model of block 208.

Figure 4:
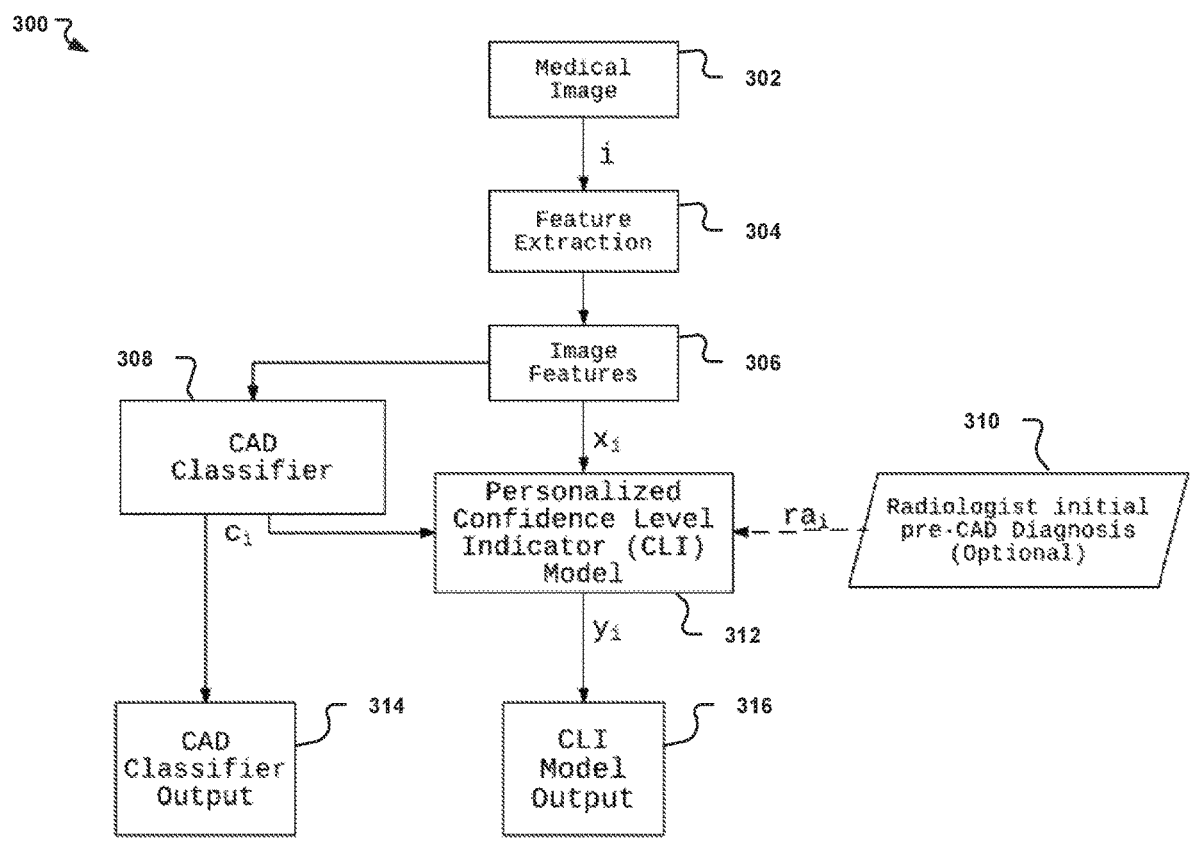
FIG. 4 is an exemplary process flow, according to aspects of the present inventive concept.

FIG. 4 is a flow chart 300 for classifying image features using the CLI model derived from FIG. 3. Similar to FIGS. 1 and 2, in block 302, a plurality of training images may be accessed from medical image database. The training images may depict areas of the human body that have characteristics that may indicate an ailment, injury, or affliction. For example, the training images may include images of a portion of a breast that need to be diagnosed to determine whether the portion shown indicates a possible cancerous region. In block 304, a feature extraction process may be implemented. In block 306, a plurality of image features may be extracted from the training images.

In block 312, a personalized confidence level indicator model may be utilized which takes as inputs a CAD classifier of block 308 and an optional radiologist initial pre-CAD diagnosis of block 310. As further shown, the CAD classifier 308 generates a CAD classifier output of block 314, and the personalized confidence level indicator model generates a CLI model output of block 316. In other words, using the personalized confidence level indicator model, a confidence level indicator can be generated for classifier outputs, or CAD system recommendations for diagnostic decisions. The confidence level indicator or CLI model output of 316 indicates how likely it is that the CAD classifier output of 314 is correct when the CAD system recommendation differs with respect to a clinician diagnostic decision. The confidence level indicator provides a confidence level similar to a probability of being correct relative to the CAD output so if the CAD system indicates that an image feature is associated with a cancerous lesion, the CLI might output, for example, 0.95 indicating that there is a 95% confidence level in the CAD diagnostic decision regarding the image feature being associated with a cancerous legion.

In one embodiment, before training a device to compute a CLI score for CAD system recommendations, a first phase of supervised machine learning may comprise training of the device to suggest classifications based on certain image features. Specifically, a fixed set of multi-dimensional feature vectors $X_i$ may be used to train the device (machine learning) to output a score $s(X_i)$ for each input vector $X_i$. The resulting trained device may then be used in operation on new data that the device was not trained on to generalize the pattern that the device learned during training (sometimes called learning).

Most supervised learning/training methods produce classifiers that output scores $s(x)$ where $s(X_i)$ is a scalar value between 0 and 1 and $X_i$ is vector of features (i.e. multiple value array) which can be used to rank the examples in the test set from the most probable member to the least probable member of a class c. That is, for two examples x and y, if $S(x)<S(y)$ (the output score given by the classifier for x is less than the score given for vector y, then $P(c/x)<P(c/y)$ (the probability that the image with feature vector x is in class C say is cancerous is less than the probability that the image with feature vector Y is in class C). However, in many applications, a ranking of examples according to class membership probability may not be enough. Most pattern recognition/machine learning systems give a relative score as to probability of class membership. The present inventive concept is operable to produce a confidence estimate (CLI score) using training data collected on a set of images along with a user model and ground truth. The method used generalizes to provide useful confidence scores on data not used in the training data. Thus a confidence or CLI score is generated which can be used to help the operator select an optimum final decision based on one or more image features presented.

In other words, the basic problem with classification is that all data values are labeled either as a "1" say for cancer or a "0" for not cancer during training. The values in between 0 and 1 are not trained as outputs of the classifier so there is much freedom as to how the intervening values are assigned to images when in actual operation. As such, only the relative ranking is related to probability of being in the class C. That is ideally one would desire an output score of >0.8 to indicate that 80% of images represented by a particular image example are cancerous but it just means that it is more likely to be cancer than image with a score of 0.7

The present inventive concept utilizes training data with intermediate values given by the human operator as well as a trained CAD system to better indicate the level of confidence of the trained CAD systems recommendation. Thus a more general value is given for the confidence (or probability of being correct) of cancer given an image with feature vector X as well as the CAD recommendation and anticipated or actual user initial decision (the operator's decision is obtained implicitly by using the CAD system which may be biased by his/her error profile) to give a confidence score of the CAD system recommendation.

In one embodiment, mathematically, a function for generating a CLI score may be described as:

P(c/X and Z and W and Q)

which reads the probability of the class being in class c given the feature vector X, with the user/operator selected a label Z, and a CAD system recommending a label W, while a known ground truth is represented by the label Q.

Labels may be cancer or not cancer, i.e., 1 or 0, respectively. Increasing specificity of an estimate by factoring information related to a user and/or a CAD system results in increased accuracy of the estimate and an improved or higher confidence score, which is specific to the user and the CAD system, thereby facilitating machine learning and processing of estimates. In other words, the function for computing the CLI score may take into account one or more specific operators and one or more specific CAD recommendation systems so that CLI scores reflect suggested confidence in CAD diagnostic decisions in the context of the one or more specific users and/or the one or more specific CAD systems.

The operator may generally assign to the ith region of interest (ROI) of the N possible ROIs in the images collected for a patient case study a score between 0 (lowest probability of cancer) to 1 (highest probability of cancer). The assigned scores are typically either 0 or 1 during operation but, for training purposes, intermediate values may be used. The operator's score may be denoted by $S1(i)$ for i=1 to N. The operator's score is the true score $S(i)$ plus the error value of the ith score denoted by $E1(i)$ where i goes from 1 to N thus $51(i)=S(i)+E1(i)$ for i=1 to N. The CAD system may be trained to give a similar output score denoted by $S2(i)=S(i)+E2(i)$ where i=1 to N. The CAD system is trained so that its errors $E2(i)$ are statistically independent of the operator's errors. Thus, if the score assigned by the operator disagrees (or is inconsistent) with the independent score of the CAD system's output score (a first assigned score is high and a second assigned score is low relative to 0.5), then a "draw condition" is detected and the optimal decision is unclear. For purposes herein, CLI can be equated to a third independent score generation device (similar to another CAD system) where $S3(i)=S(i)+E3(i)$. The CLI may be designed so that its errors $E3(i)$ where i=1 to N are statistically independent of both the operator's errors $E1(i)$ i=1 to N and the first CAD systems errors $E2(i)$ i=1 to N. Thus its output can be used as an independent opinion, e.g., to break a draw condition when such arises between the operator and the first CAD system by using a simple majority rule voting logic, i.e., if 2 out of the 3 scores are high, then select high, or if 2 out of three scores are low, then select low. Alternative logic such as trim means can be used on the three independent scores to get enhanced performance over the operator's unaided performance. The first CAD system may encompass CAD systems that have been trained to generate recommendations in some form, but have not been enhanced with CLI functionality as discussed herein.

The system of the present inventive concept allows an operator to correct their error if they rely on the CAD system/device and follow its recommendation over their own, e.g., when it is correct and they are incorrect. One unique aspect is the initial training of the device, as disclosed by U.S. patent application Ser. No. 15/200,719, is that the device is trained specifically to variably weigh errors made by an individual and/or group of operators, e.g., more heavily, to ensure that CAD system recommenders give correct recommendations when the operator is most likely to need help in correcting an unaided recommendation of the operator.

The present inventive concept is operable to select and utilize one or more classifiers that are diverse from each to optimize their combined decision. U.S. patent application Ser. No. 15/200,719 discloses a new method and means to obtain a personalized diverse classifier which provides a recommendation that can be combined with the operator's initial recommendation to improve the operator's accuracy by correcting one or more of their errors when the operator elects to accept the recommendation(s) at the appropriate time(s).

The present inventive concept teaches a new way to combine the recommendations from the trained CAD system of U.S. patent application Ser. No. 15/200,719 with an operator's initial recommendation so as to improve the accuracy of the final decision or recommendation; and the operator also learns to select the CAD recommendations when the confidence level is high (much greater than 0.5) of the CD! score and this reassessment may correct the operator's initial incorrect assessment. In addition, the CLI system may provide a low confidence level (much lower than 0.5) when the operator is probably better off not to follow the CAD recommendation and proceed with their initial assessment.

Figure 5:
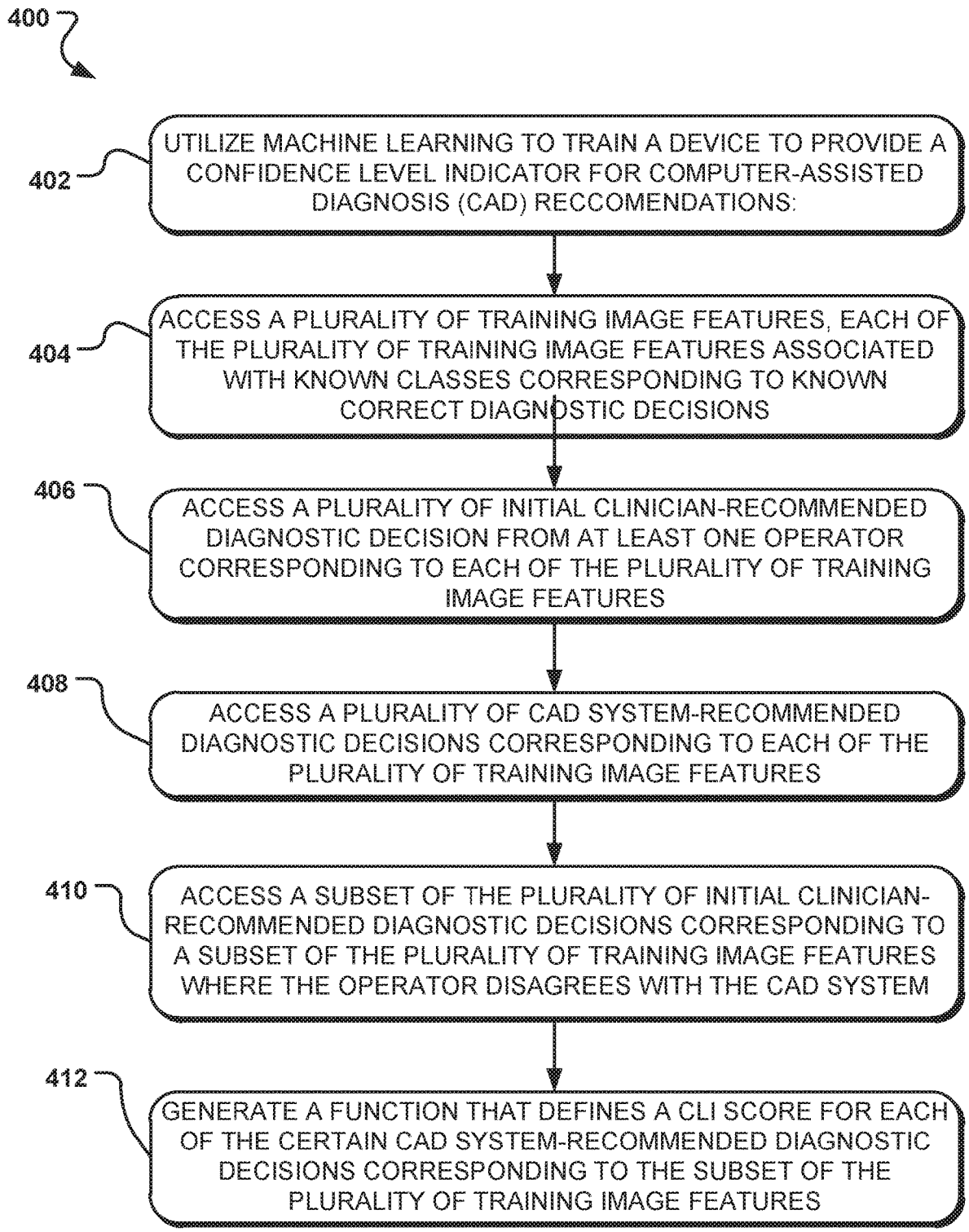
FIG. 5 is an exemplary process flow, according to aspects of the present inventive concept.

FIG. 5 is a process flow 400 for generating a CLI model to be utilized with CAD system recommendations for diagnostic decisions. In block 402, machine learning may be utilized or otherwise implemented by a device to provide a confidence level indicator (CLI) for CAD recommended diagnostic decisions that are generated from the subject device or other devices. Where the device itself has already been initially trained to generate recommendations as to diagnostic decisions for image features accessed by the device, the device may have been trained using initial machine learning as set forth in the related U.S. patent application Ser. No. 15/200,719 incorporated by reference. Thus, in one embodiment, utilizing machine learning to train the device to provide a CLI may be an improvement upon a CAD system already trained to recommend diagnostic decisions; and, the same device/application may be modified to take into account the functionality (functions/algorithms) used to generate the CLI score.

In block 404, the device may access a plurality of training image features. Each of the training image features may be associated within known classes. In other words, certain image features may be associated with a lesion that has been proven as being cancer. In other cases, certain image features have been proven to be non-cancerous. In either case, all of the training image features are already assigned to one clinical class or another, based on evidence, proven test results, or the like. The classes may correspond to classes of an IRADS system as described in the related U.S. patent application Ser. No. 15/200,719.

In block 406, a plurality of initial clinician-recommended diagnostic decisions from at least one operator are accessed. Each of the decisions may be made to diagnose one or more of the training image features (the true or known results of which are unknown to the operator). The operator's diagnostic decision or interpretation of the training image data may be obtained using a variety of methods. For example, direct labels consensus labels, operator models, multi-operator models, fine-tuned operator models, and/or archetypical operator models may be utilized as explained herein (although the disclosure is not limited to such models and additional models are contemplated).

In block 408, a plurality of CAD system-recommended diagnostic decisions may be accessed for each of the plurality of training image features. Where the subject device is the same computing device/CAD system that was initially trained to make CAD system diagnostic decisions, the device may simply apply the methodology and functions used during the initial training with the training images to compute such CAD system-recommended diagnostic decisions for each of the plurality of training image features.

In block 410, the device may access a subset of the plurality of initial clinician recommended diagnostic decisions corresponding to a subset of the plurality of training image features. The subset being where the operator disagrees or otherwise provides a diagnostic decision that is not consistent with or is different than the CAD system diagnostic decision for one or more certain training image features.

In some embodiments, it may be determined at this step whether the operator/clinician changes his/her diagnostic decision when taking into account the CAD system recommended diagnostic decision. For example, in some cases, the operator will produce a diagnostic decision for a training image feature, and then may change that decision when provided with a CAD system-recommended diagnostic decision for the same training image feature. Such data may be aggregated for the operator and may be utilized as part of a function to compute a CLI score.

In block 412, a function may be generated that defines a CLI score for each of the certain CAD system-recommended diagnostic decisions corresponding to the subset of the plurality of training image features. In other words, one or more functions can be generated that compute CLI scores for certain CAD recommendation system diagnostic decisions where the operator has disagreed with such certain CAD recommendation system diagnostic decisions.

Figure 6:
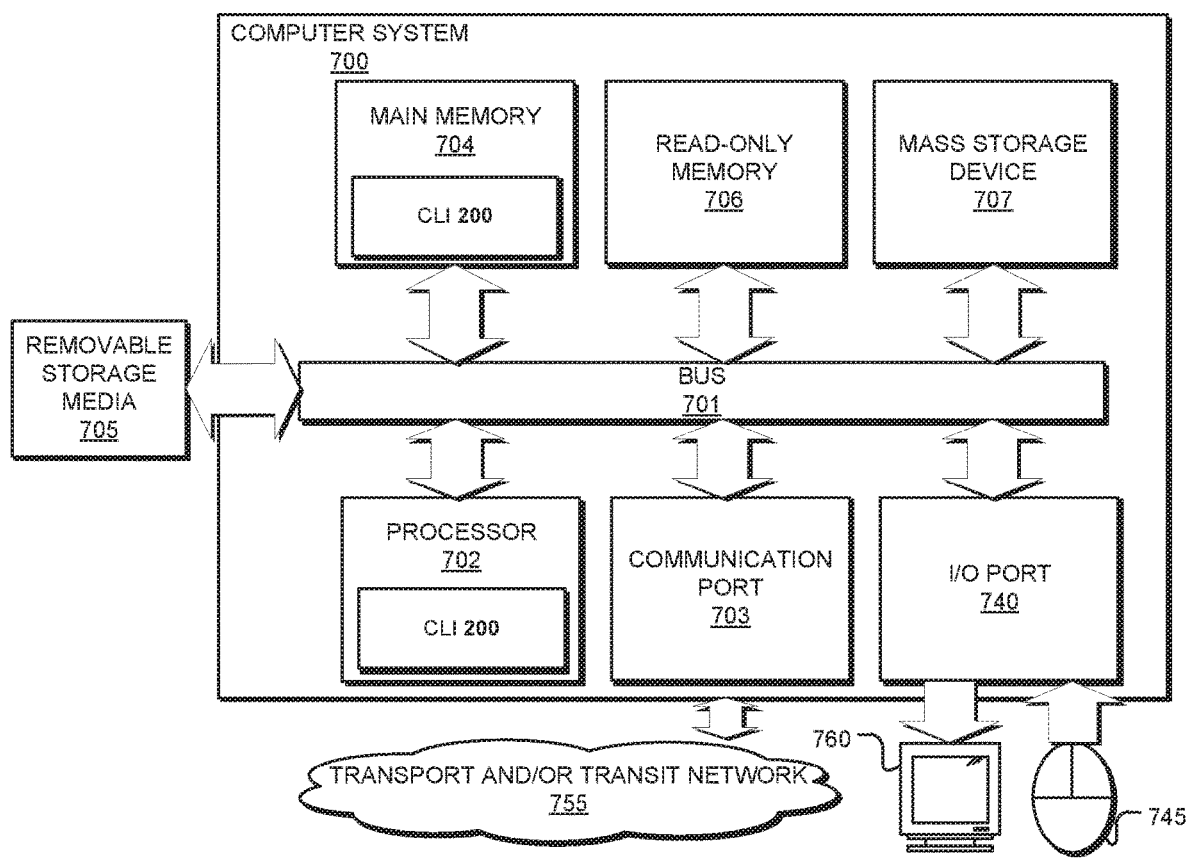
FIG. 6 is an exemplary computing system that may implement various services, systems, and methods discussed herein.

FIG. 6 is an example schematic diagram of a computing system 700 that may implement various methodologies discussed herein. For example, the computing system 700 may comprise a computing device used to implement a CLI application 70 for generating CLIs or CLI scores for certain CAD system recommendations. The computing system 700 includes a bus 701 (i.e., interconnect), at least one processor 702 or other computing element, at least one communication port 703, a main memory 704, a removable storage media 705, a read-only memory 706, and a mass storage device 707. Processor(s) 702 can be any known processor, such as, but not limited to, an Intel® Itanium® or Itanium processor(s), AMD® Opteron® or Athlon MP® processor(s), or Motorola® lines of processors. Communication port 703 can be any of an RS-232 port for use with a modem based dial-up connection, a 10/100 Ethernet port, a Gigabit port using copper or fiber, or a USB port. Communication port(s) 703 may be chosen depending on a network such as a Local Area Network (LAN), a Wide Area Network (WAN), or any network to which the computer system 200 connects. Computing system may further include a transport and/or transit network 755, a display screen 760, an I/O port 740, and an input device 745 such as a mouse or keyboard.

Main memory 704 can be Random Access Memory (RAM) or any other dynamic storage device(s) commonly known in the art. Read-only memory 706 can be any static storage device(s) such as Programmable Read-Only Memory (PROM) chips for storing static information such as instructions for processor 702. Mass storage device 707 can be used to store information and instructions. For example, hard disks such as the Adaptec® family of Small Computer Serial Interface (SCSI) drives, an optical disc, an array of disks such as Redundant Array of Independent Disks (RAID), such as the Adaptec® family of RAID drives, or any other mass storage devices, may be used.

Bus 701 communicatively couples processor(s) 702 with the other memory, storage, and communications blocks. Bus 701 can be a PCI/PCI-X, SCSI, or Universal Serial Bus (USB) based system bus (or other) depending on the storage devices used. Removable storage media 705 can be any kind of external hard drives, thumb drives, Compact Disc-Read Only Memory (CD-ROM), Compact Disc-Re-Writable (CD-RW), Digital Video Disk-Read Only Memory (DVD-ROM), etc.

Embodiments herein may be provided as a computer program product, which may include a machine-readable medium having stored thereon instructions which may be used to program a computer (or other electronic devices) to perform a process. The machine-readable medium may include, but is not limited to optical discs, CD-ROMs, magneto-optical disks, ROMs, RAMs, erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments herein may also be downloaded as a computer program product, wherein the program may be transferred from a remote computer to a requesting computer by way of data signals embodied in a carrier wave or other propagation medium via a communication link (e.g., modem or network connection).

As shown, main memory 704 is encoded with a CLI application 70 that supports functionality as discussed herein. The CLI application 70 (and/or other resources as described herein) can be embodied as software code such as data and/or logic instructions (e.g., code stored in the memory or on another computer readable medium such as a disk) that supports processing functionality according to different embodiments described herein. During operation of one embodiment, processor(s) 702 accesses main memory 704 via the use of bus 701 in order to launch, run, execute, interpret, or otherwise perform processes, such as through logic instructions, executing on the processor 702 and based on the CLI application 70 stored in main memory or otherwise tangibly stored.

The description above includes example systems, methods, techniques, instruction sequences, and/or computer program products that embody techniques of the present disclosure. However, it is understood that the described disclosure may be practiced without these specific details. In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic instructions.

Additional aspects, advantages, and utilities of the present inventive concept will be set forth in part in the present description and drawings and, in part, will be obvious from the present description and drawings, or may be learned by practice of the present inventive concept.

The present description and drawings are intended to be illustrative and are not meant in a limiting sense. Many features and sub-combinations of the present inventive concept may be made and will be readily evident upon a study of the present description and drawings. These features and sub-combinations may be employed without reference to other features and sub-combinations.

The invention claimed is:

1. An apparatus, comprising:
a memory; and
a processor operatively coupled to the memory, the processor configured to:
  obtain a plurality of known diagnostic decisions, each known diagnostic decision from the plurality of known diagnostic decisions associated with at least one image feature from a plurality of image features and validated based on non-imaging data of at least one tissue portion associated with the at least one image feature;
  receive diagnostic labels for a set of training images from a set of users;
  construct a model for generating simulated labels for training images based on the diagnostic labels for the set of training images;
  generate, for each training image from a plurality of training images, a simulated label using the model for generating simulated labels, the plurality of training images associated with the plurality of image features;
  determine a plurality of user-recommended diagnostic decisions for the set of users based on the simulated label for each training image from the plurality of training images, each user-recommended diagnostic decision from the plurality of user-recommended diagnostic decisions associated with at least one image feature from the plurality of image features;
  obtain a plurality of computer-assisted diagnosis (CAD) system-recommended diagnostic decisions provided by a CAD system, each CAD system-recommended diagnostic decision from the plurality of CAD system-recommended diagnostic decisions associated with at least one image feature from the plurality of image features;

construct a model for generating confidence level indicators (CLIs) of CAD system-recommended diagnostic decisions for regions of interest (ROIs) based on the plurality of known diagnostic decisions, the plurality of user-recommended diagnostic decisions, and the plurality of CAD system-recommended diagnostic decisions;

receive a CAD system-recommended diagnostic decision for a ROI; and generate a CLI for the CAD system-recommended diagnostic decision using the model, the CLI indicative of a likelihood of the CAD system-recommended diagnostic decision being reflective of a true diagnostic decision for the ROI.

2. The apparatus of claim 1, wherein the processor is configured to construct the model for generating CLIs by:

defining a function that provides a probability of a set of image features from the plurality of image features belonging to a class from a plurality of classes given (1) a user-recommended diagnostic decision associated with the set of image features and from the plurality of user-recommended diagnostic decisions, (2) a CAD system-recommended diagnostic decision associated with the set of image features and from the plurality of CAD system-recommended diagnostic decisions, and (3) a known diagnostic decision associated with the set of image features and from the plurality of known diagnostic decisions.

3. The apparatus of claim 1, wherein the plurality of image features is a first plurality of image features, and the processor is configured to obtain the plurality of CAD system-recommended diagnostic decisions by:

receiving a plurality of training images, each training image from the plurality of training images associated with a known class selected from a plurality of classes and validated based on non-imaging data of a tissue portion associated with that training image;

extracting a second plurality of image features from the plurality of training images;

constructing a model for generating CAD system-recommended diagnostic decisions based on the second plurality of image features and the known class associated with each training image from the plurality of training images; and generating the plurality of CAD system-recommended diagnostic decisions using the model for generating CAD system-recommended diagnostic decisions.

4. The apparatus of claim 1, wherein the non-imaging data includes biopsy data of a plurality of tissue portions, and the plurality of user-recommended diagnostic decisions further includes diagnostic decisions made by the set of users based on viewing images of the plurality of tissue portions.

5. The apparatus of claim 1, wherein the plurality of image features includes pixel values associated with images of a plurality of tissue portions.

6. An apparatus, comprising:

a memory; and a processor operatively coupled to the memory, the processor configured to:

receive a set of known classes for a plurality of training image features, each known class from the set of known classes selected from a plurality of classes and validated based on non-imaging data of a tissue portion associated with at least one training image feature from the plurality of training image features;

receive a set of user-recommended classes for the plurality of training image features, each user-recommended class from the set of user-recommended classes selected from the plurality of classes and selected by a user based on viewing at least one training image feature from the plurality of training image features;

identify discrepancies between the set of known classes and the set of user-recommended classes;

construct a user-specific model for identifying one or more image features for which a user-recommended class would differ from a known class based on the discrepancies identified between the set of known classes and the set of user-recommended classes;

receive a set of computer-assisted diagnosis (CAD) system-recommended classes for the plurality of training image features, each CAD system-recommended class from the set of CAD system-recommended classes selected from the plurality of classes and generated by a model trained using the plurality of training image features; and construct a confidence level indicator (CLI) model for generating a CLI of a CAD system-recommended class selected from the plurality of classes and associated with a region of interest (ROI), the model constructed based on the set of known classes for the plurality of training images, the set of user-recommended classes for the plurality of training image features, the user-specific model, and the set of CAD system-recommended classes for the plurality of training image features, the CLI indicative of a likelihood of the CAD system-recommended class being reflective of a true class for the ROI.

7. The apparatus of claim 6, wherein the set of CAD system-recommended classes is a first set of CAD system-recommended classes, and the processor is further configured to:

receive a second set of CAD system-recommended classes associated with a set of ROIs; and generate, for each CAD system-recommended class from the second set of CAD system recommended classes, a CLI for that CAD system-recommended class using the CLI model, the CLI for a first CAD system-recommended class from the second set of CAD system recommended classes being different from a second CAD system-recommended class from the second set of CAD system recommended classes.

8. The apparatus of claim 6, wherein the processor is further configured to:

receive a set of training images including the plurality of training image features;

extract the plurality of training image features from the set of training images; and present the plurality of training image features to the user such that the user, in response to viewing the plurality of training image features, can provide the set of user-recommended classes for the plurality of training image features.

9. The apparatus of claim 6, wherein the set of user-recommended classes is a set of pre-CAD viewing user-recommended classes and the user-specific model is a pre-CAD user-specific model, the processor is further configured to:

present the set of CAD system-recommended classes for the plurality of training image features to the user;

receive a set of post-CAD viewing user-recommended classes for the plurality of training image features after presenting the set of CAD system-recommended classes for the plurality of training image features to the user, the set of post-CAD viewing user-recommended classes being selected by a user based on viewing (1) the plurality of training image features and (2) the set of CAD system-recommended classes for the plurality of training image features;

identify discrepancies between the set of known classes and the set of post-CAD viewing user-recommended classes; and construct a post-CAD user model for identifying one or more image features for which a post-CAD viewing user-recommended class from the set of post-CAD viewing user-recommended classes would differ from a known class from the set of known classes based on the discrepancies identified between the set of known classes and the set of post-CAD viewing user-recommended classes, the processor configured to construct the CLI model further based on the set of post-CAD viewing user-recommended classes and the post-CAD user model.

10. The apparatus of claim 6, wherein the processor is configured to construct the user model by adapting, based on the discrepancies identified between the set of known classes and the set of user-recommended classes, a general model constructed for a plurality of users.

11. The apparatus of claim 6, wherein the plurality of image features includes pixel values associated with images of a plurality of tissue portions.

12. The apparatus of claim 6, wherein the plurality of classes are categories of an image reporting and data system (I-RADS).

13. The apparatus of claim 1, wherein the plurality of training images includes a larger set of training images than the set of training images.

14. The apparatus of claim 1, wherein the plurality of training images includes the set of training images.

* * * * *